US005795710A

United States Patent [19]

Park

[11] Patent Number: 5,795,710
[45] Date of Patent: Aug. 18, 1998

[54] METHOD AND APPARATUS FOR ORGAN CULTURE

[76] Inventor: Sung-Su Park, Cheonggu Apt. 103-1306, #929 Mok 6-dong, Yangcheon-gu, Seoul, Rep. of Korea, 158-056

[21] Appl. No.: 788,253

[22] Filed: Jan. 27, 1997

Related U.S. Application Data

[62] Division of Ser. No. 555,600, Nov. 9, 1995.

[30] Foreign Application Priority Data

Nov. 9, 1995 [KR] Rep. of Korea ............ 94-29214

[51] Int. Cl.$^6$ ............... A01N 1/02; C12P 1/00
[52] U.S. Cl. ............ 435/1; 435/326; 435/325; 435/366; 435/368; 435/394; 435/395; 435/41
[58] Field of Search ............ 435/326, 325, 435/366, 370, 368, 394, 395, 41, 1

[56] References Cited

U.S. PATENT DOCUMENTS 3,450,598  6/1969  Welsh et al. ............ 195/1.8
3,827,943  8/1974  Forbes et al. ............ 195/127
5,585,266  12/1996  Plitt et al. ............ 435/240.23

OTHER PUBLICATIONS

Saneto et al. "Neuronal and glial cells: cell culture of the central nervous system". In: Neurochemistry: a practical approah. IRL Press Limited, Oxford, England, pp. 27–63, 1987.

Smith et al. Life Sciences 36(14): 1367–1375, 1985.

*Primary Examiner*—Marian C. Knode
*Assistant Examiner*—Jay F. Williams
*Attorney, Agent, or Firm*—Anderson Kill & Olick, P.C.

[57] ABSTRACT

A method for culturing an organic tissue comprising: attaching the tissue onto an inner side of a mesh which is placed in an incubation chamber, and culturing the tissue in the presence of a culture medium and a gas containing oxygen under a condition that the ratio of the contact time of the tissue with the culture medium to that with the gas lies in a range from 1:2.5 to 1:3.5.

4 Claims, 5 Drawing Sheets

METHOD AND APPARATUS FOR ORGAN CULTURE

This is a divisional application of Ser. No. 07/555,600, filed Nov. 9, 1995.

FIELD OF THE INVENTION

The present invention relates to a method for culturing an organic tissue, and also to apparatus for carrying out the method. Specifically, it pertains to: a method for culturing an organic tissue, wherein the tissue is attached onto an inner side of a mesh which is placed in an incubation chamber, and cultured in the presence of both a culture medium and a gas containing oxygen under a condition that the ratio of the contact time of the tissue with the culture medium to that with the gas ranges from 1:2.5 to 1:3.5; an apparatus for carrying out the method; and a process for producing antibodies or culturing hepatitis B virus using the apparatus.

BACKGROUND OF THE INVENTION

The recent progress in the cell culture technique has made it possible to carry out in vitro experiments using various cell cultures. However, a cell culture does not normally provide information on the structural organization of an organ or the interrelationship between cells and connective tissues. In order to complement the cell culture methods, therefore, various organ culture methods, and suitable apparatus therefor, capable of providing such structural information of cells and/or tissues have been developed and reported.

A static organ culture method has been reported by Trowell, O. A., *Experimental Cell Research*, 16, 118(1959), in which a slice of an organ, e.g., liver, is placed on a filter and the filter is wetted with a culture medium so as to supply the organ with the medium by diffusion, while oxygen is supplied to the organ by exposing to air the organ surface opposite the part attached to the filter. An organ culture apparatus using the above method has, however, experienced a number of problems including: central necrosis caused by the deficiency of oxygen supply is observed because the culture tissue in this system is divided into a gas-tissue interface and a medium-tissue interface; the thickness and the size of the tissue slice to be cultured is restricted; and it cannot be used for the culture of adult tissues because it is adapted for culturing organs of fetal stage that are actively proliferating and differentiating. Further, this apparatus is not suitable for the culture of certain organs, e.g., liver, which have a high oxygen demand due to their high activity in both metabolism and material synthesis.

Figure 1A:
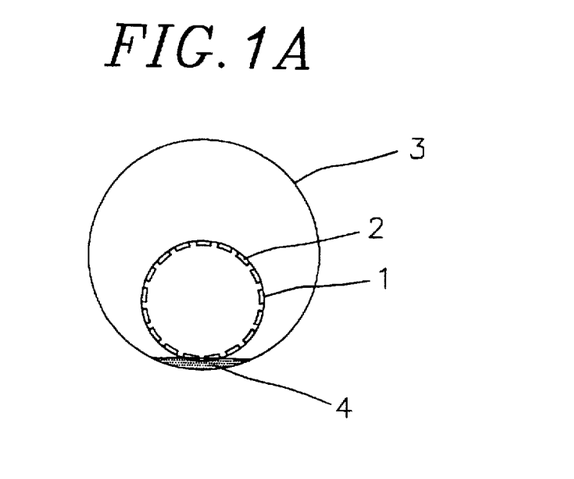
FIG. 1 shows a schematic illustration of the principle of the prior dynamic organ culture apparatus.
Figure 1B:
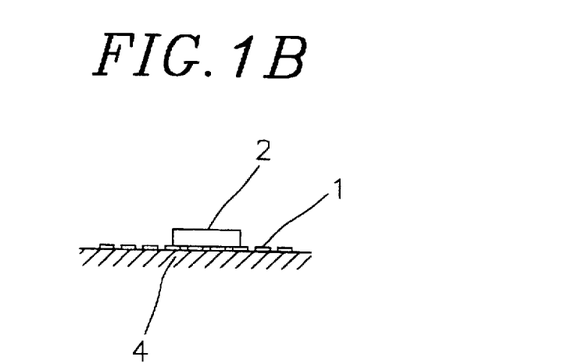

To ameliorate the above problems, especially the problem of central necrosis, Smith, P. F., et al. have proposed an apparatus called dynamic organ culture system, which is illustrated in FIG. 1 (see, for further information, *Life Sciences*, 36, 1367(1985)). In this system, a slice of organ 2 is placed on a cylindrical mesh 1 and loaded in an incubation chamber 3, e.g., a glass vial, and then, a suitable amount of culture medium 4 is introduced to the incubation chamber 3 as shown in FIGS. 1(A) and 1(B). The incubation chamber 3 is then capped, and rotated by a suitable means, while a 95% $O_2$/5% $CO_2$ gas mixture is supplied. As the incubation chamber 3 rotates, the organ slice is exposed alternatively to the medium-tissue interface and the gas-tissue interface, so that the central necrosis caused by oxygen deficiency can be suppressed.

Figure 1C:
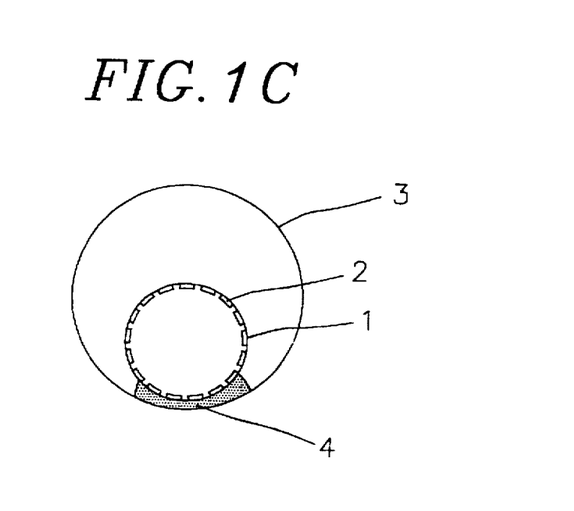

However, this apparatus has the problem that the cylindrical mesh 1 does not rotate smoothly because of the surface tension between the glass wall of the incubation chamber 3 and the culture medium 4, as shown in FIG. 1(C). Another problem with this apparatus is that frequent medium exchange is required due to a limited medium-receiving capacity of the system which is limited by the contact space between the cylindrical mesh 1 and the glass incubation chamber 3 in the lower part of the chamber. In addition, it is well known that the viability of cells increases if the incubation chamber is pressurized with a gas during the course of the culture. However, the above system is not designed for a pressurized operation. Further, the above system is unreliable in that, although the viability of the tissue culture has been tested in biochemical terms, the viability in morphological terms and the optimum culture condition remain unsettled.

Therefore, there has continued to exist a need for a reliable and effective method for organ culture.

SUMMARY OF THE INVENTION

Accordingly, it is an object of the present invention to provide a method for culturing various organic tissues, which is limited neither by the tissue size nor by the problem of central necrosis.

Another object of the present invention is to provide an apparatus for carrying out the method.

A further object of the present invention is to provide methods of culturing a liver or a central nervous tissue or hepatitis B virus and producing monoclonal or polyclonal antibodies using the tissue culture apparatus.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

In accordance with the present invention, there is provided a method for culturing an organic tissue comprising: attaching the tissue onto an inner side of a mesh which is placed in an incubation chamber, and culturing the tissue in the presence of a culture medium and a gas containing oxygen under a condition that the ratio of the contact time of the tissue with the culture medium to that with the gas lies in a range from 1:2.5 to 1:3.5.

The method of the present invention can be carried out using either a dynamic or a static culture apparatus. In the method of the present invention using a dynamic culture system, an organic tissue is brought into contact alternately with a culture medium and a gas by changing the position of the tissue by rotation, while maintaining the position of the medium stationary. On the other hand, in the method of the present invention using a static culture system, the organic tissue is brought into contact alternately with a culture medium and a gas by introducing the medium intermittently at regular intervals, while maintaining the culture tissue stationary.

The method of the present invention will be described in detail in connection with the preferable embodiment of the apparatus for carrying out the method.

The dynamic culture system of the present invention comprises a horizontal cylindrical incubation chamber; a square pillar-formed mesh which closely fits the interior of the chamber; means to rotate the chamber; and means for supplying a sterilized gas to the chamber.

Figure 2:
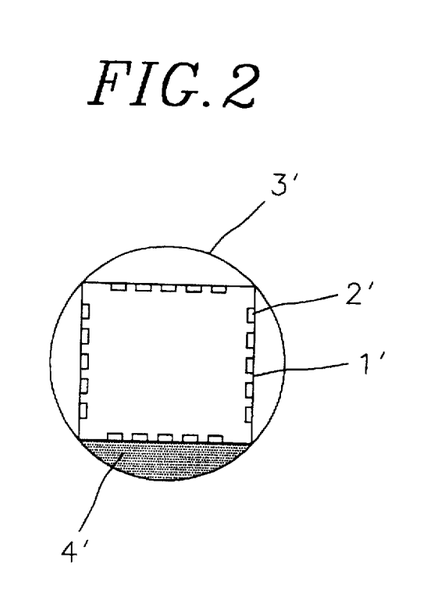
FIG. 2 depicts a schematic view of the principle of the dynamic organ culture apparatus of the present invention.

FIG. 2 is a schematic diagram that illustrates the principle of the dynamic organ culture system of the present invention, wherein a culture tissue 2' is attached to an inner side of a square pillar-formed mesh 1' which closely fits the interior of a cylindrical chamber 3', and a culture medium 4' is supplied to fill one of the four spaces formed between the cylindrical mesh 1' and the incubation chamber 3'. As the cylindrical incubation chamber rotates, the tissue on the mesh alternately contacts the medium and the gas in a contact time ratio of 1:3, i.e., the contact time of the tissue with the gas is three times that with the medium. This apparatus can thus be used for culturing an organic tissue which has a high oxygen demand, e.g., a liver tissue, without risking necrosis of the tissue caused by oxygen deficiency.

Figure 3:
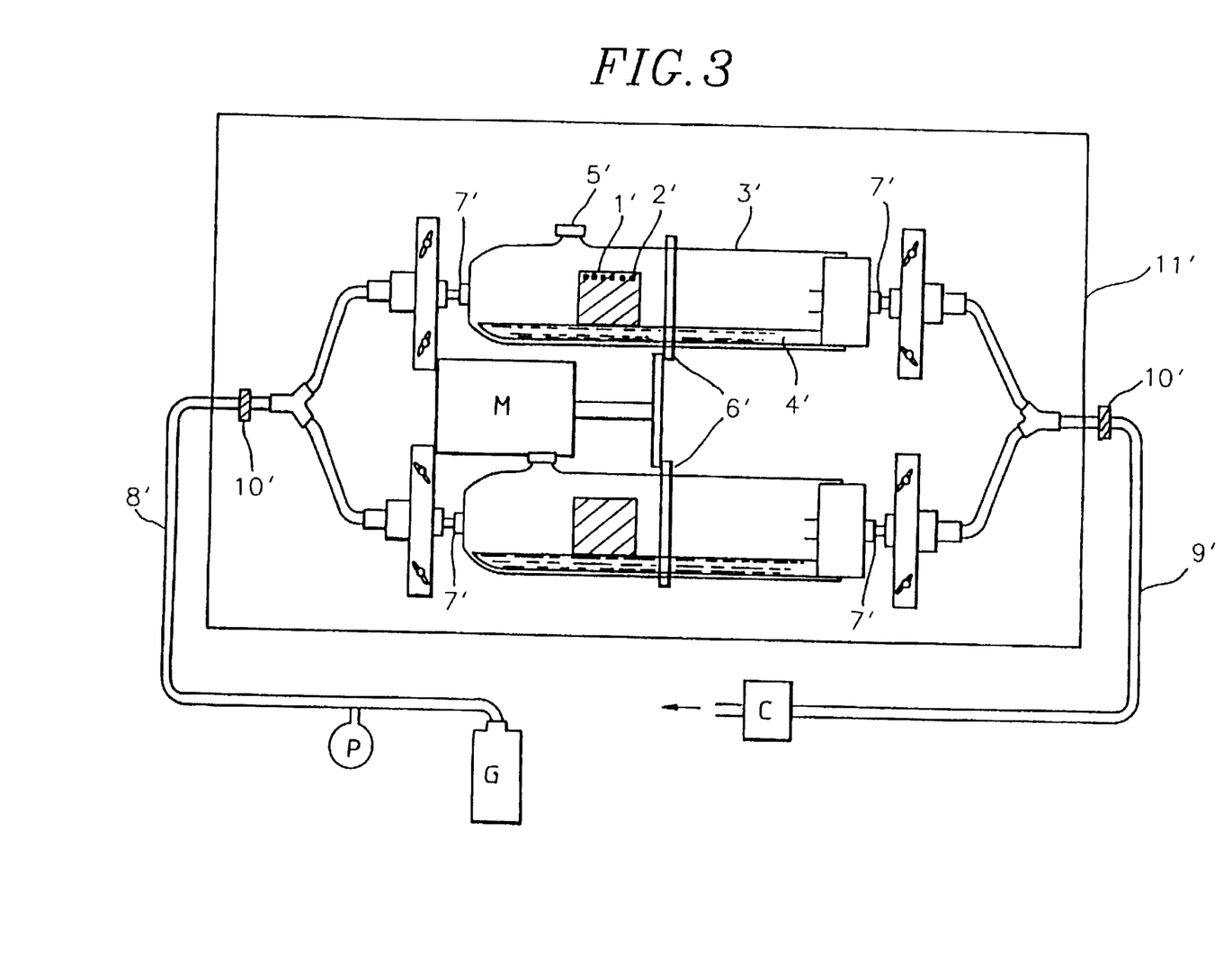
FIG. 3 displays an embodiment of the dynamic organ culture apparatus of the present invention.

FIG. 3 is a schematic diagram that illustrates an embodiment of the dynamic organ culture apparatus of the present invention. As can be seen from FIG. 3, an organic tissue 2' is attached to an inner part of a square pillar-formed mesh 1' which is placed in the interior of a cylindrical incubation chamber 3'. Culture medium 4' is introduced to the bottom of the incubation chamber 3' as shown in FIG. 2. The incubation chamber 3' is made of pyrex glass, which can bear a pressure of more than 3 atm and can be autoclaved, and it is equipped with a cap 5' for introducing the medium and sampling. Mesh 1' is made of stainless steel and its mesh size preferably ranges from 200 to 400 µm.

A gas-tight rotational joint 7' connects the cylindrical incubation chamber 3' with a gas inlet line 8' or a gas outlet line 9', and the cylindrical incubation chamber 3' is rotated at a rate of 5 to 8 rpm by means of the motor M and a rotational gear 6', and thereby, the organic tissue 2' on mesh 1' alternately contacts the medium 4' and the gas.

The gas G, which is preferably a mixture of 95% by volume $O_2$ and 5% by volume $CO_2$, is introduced at a pressure as high as 3 atm into the incubation chamber 3' through the gas inlet line 8' and discharged therefrom through the gas outlet line 9'. A solenoid valve which is coupled with a controller C controls and maintains the set gas pressure.

A gas sterilizing device 10', i.e., a syringe filter having a pore size of 0.22 µm, is installed in the middle of the gas supplying line 8' to filter out the microbes, thereby sterilizing the supply gas to the incubation chamber 3'. Another gas sterilizing device is preferably installed in the gas outlet line 9' in order to prevent the backflow of microbes in the atmospheric gas.

The incubation chamber 3' is maintained at a constant temperature which is adjusted according to the type of the tissue to be cultured, e.g., 37°±0.5° C. for human liver tissues, and 38°±0.2° C., for rat or dog tissues.

The number of the incubation chamber may be varied in accordance with the amount and objects of the culture, and more than one mesh can be placed in one incubation chamber, while FIG. 3 shows an embodiment of the culture apparatus wherein two incubation chambers each containing only one mesh are installed.

As described above, the dynamic organ culture apparatus of the present invention has several advantages: it is an enclosed system equipped with an automated gas supply and high pressure control, which enables an efficient culture of tissues; it can be used at a high pressure of 3 atm. or more, in contrast to the apparatus of the prior art whose use cannot succeed 1.5 atm. and therefore, a much higher viability of cells can be maintained during the culture; it is free from the problem of the prior art, i.e., the rotation of the mesh is not interrupted by the surface tension between the glass incubator and the medium, frequent medium exchange is not necessary, and an increased amount of tissues can be cultured at one time; and a tissue of increased thickness of 200–500 µm, as opposed to 150–300 µm of the prior art, can be cultured without risking central necrosis.

On the other hand, the static culture apparatus of the present invention comprises a sealable erect incubation chamber; a mesh which is installed along an inner wall of the chamber at a fixed distance from the wall; a medium reservoir connected to the bottom of the incubation chamber; means for supplying a culture medium, which extends from the medium reservoir to a space between an upper inner wall of the incubation chamber and the mesh; means for regulating the supply of the culture medium; and means for supplying a sterilized gas to the incubation chamber.

In the static culture apparatus of the present invention, a mesh is installed along the inner wall of the erect incubation chamber at a fixed distance from the wall and a desired tissue is attached to an inner side of the mesh. The medium is supplied through the space between the incubation chamber and the mesh along the inner side of the incubation chamber at regular intervals, then it runs down through the space between the inner wall of the incubation chamber and the mesh. The tissue on the mesh contacts the medium while the medium is flowing down, but it contacts the gas while the medium supply is interrupted. Therefore, the tissue alternately contacts the medium and the gas at regular intervals.

The medium which has flown down to the bottom of the incubation chamber is collected in a medium reservoir installed at the bottom of the incubation chamber, and the collected medium is recirculated to the upper inner wall of the incubation chamber. The time interval of the medium supply is regulated so as to maintain the ratio of the contact time of the tissue with the medium to that with the gas within a range of 1:2.5 to 1:3.5. Owing to the intermittent supply of the medium as described above, the culture tissues are evenly supplied with nutrients in the medium and they, although in a static state, do not suffer from central necrosis.

Figure 4:
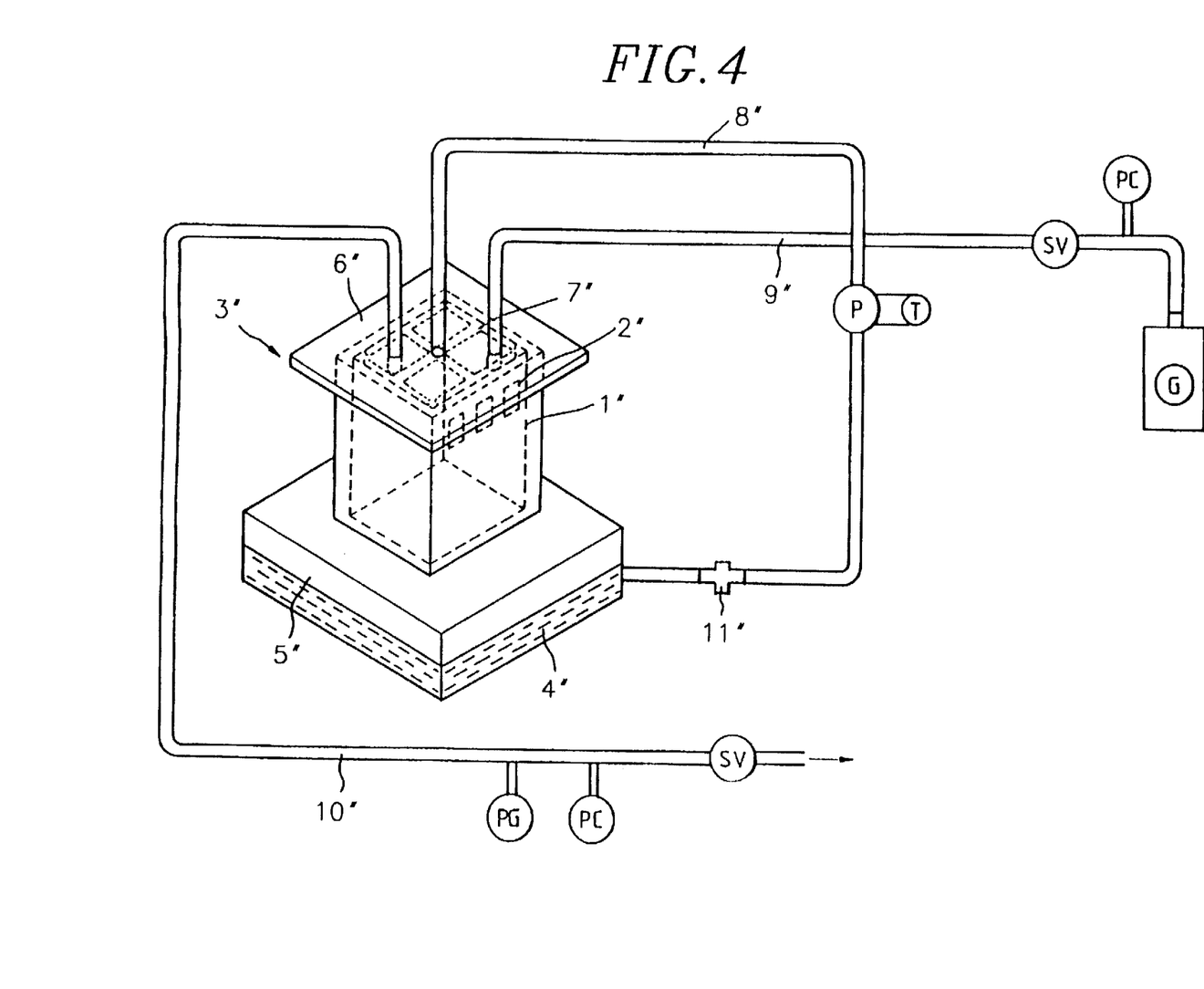
FIG. 4 exhibits an embodiment of the static organ culture apparatus of the present invention.
Figure 5A:
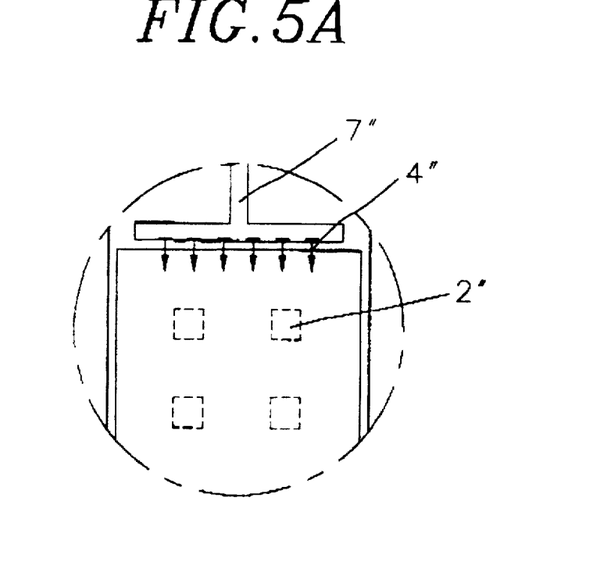
FIG. 5A shows a schematic diagram of the section of the static apparatus of the present invention, where the medium supplying line is in contact with the inner wall of the incubation chamber.
Figure 5B:
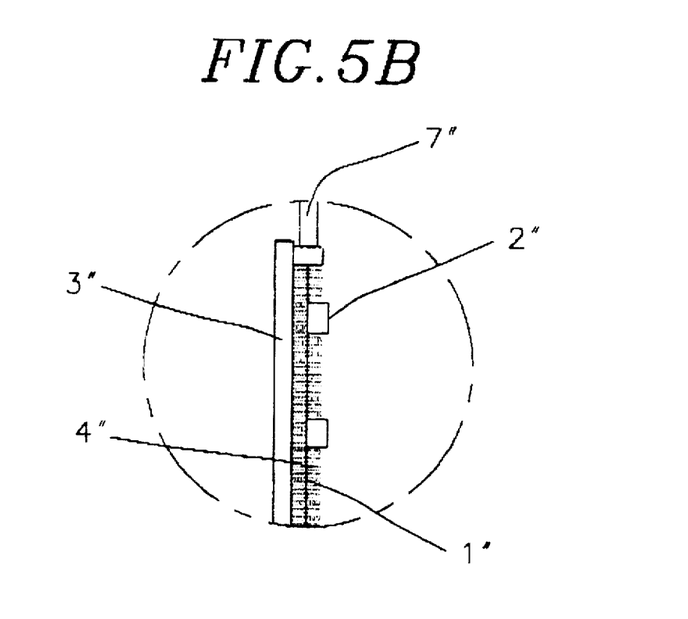
FIG. 5B, a cross-sectional view of this section.

FIG. 4 exhibits an embodiment of the static organ culture apparatus of the present invention, and FIG. 5 A illustrates the section of the static apparatus where the medium supplying line is in contact with the inner wall of the incubation chamber, and FIG. 5B, a cross-sectional view of this section.

The method of the present invention will be described in detail in conjunction with the preferable embodiment of the static tissue culture apparatus of the present invention as shown in FIGS. 4 and 5.

In the static culture system of the present invention, a mesh 1" is installed along an inner wall of a sealable erect incubation chamber 3" at a fixed distance, i.e., 2–3 mm, from the wall, and a desired organic tissue 2" is placed onto an inner side of the mesh 1".

The shape of the erect incubation chamber 3" may be one of various pillar forms, e.g., a square or a cylindrical pillar form, whose inner wall may be erect or slant. When culturing a tissue which is hardly adhesive to the mesh due to its lipid contents, it is preferable to make the inner wall of the incubation chamber 3" slanted inward so that the width of the incubation chamber 3" decreases gradually toward the bottom, which is effective in preventing the removal of the tissue from the mesh being swept by the downward stream of the medium.

Mesh 1' is made of stainless steel of a square or a cylindrical pillar form, and its mesh size preferably ranges from 200 to 400 µm.

The incubation chamber 3" may be a square pillar covered with an upper plate 6" equipped with a medium supplying line and gas flow lines, or it may be a sealed single body with built-in lines. A medium 4" is supplied intermittently at regular intervals from a medium reservoir 5" to the top of the incubation chamber 3", through a medium supplying line 8". The medium supplying line 8" may be diverged into a number of medium supplying ducts 7", each of which is located in the upper part of the space between the mesh 1" and the inner wall of the incubation chamber 3". The medium supplying duct 7" is preferably positioned so that about ⅘ of the supplied medium is run down between the inner wall of the incubation chamber 3" and the mesh 1" and about ⅕ of the supplied medium is run down along the surface of the mesh 1", as illustrated in FIG. 5(B). Further, as shown in FIG. 5(A), the end of the medium supplying duct 7" may be a spray-type so that the medium 4" may be evenly supplied over the entire surface of the mesh 1".

The medium which is supplied to the top of the incubation chamber 3" through the medium supplying duct 7" runs down through the incubation chamber 3" and then collected in the medium reservoir 4" installed at the bottom of the incubation chamber 3". When the level of the collected medium becomes higher than a set point, the medium is recirculated to the top of the incubation chamber 3" through the medium supplying line 8". A peristaltic pump P with a timer T is installed in the medium supplying line 8" in order to control the medium supplying interval so that the ratio of the contact time of the tissue with the medium to that with the gas lies in a range from 1:2.5 to 1:3.5.

The gas G, which is preferably a mixture of 95% by volume $O_2$ and 5% by volume $CO_2$, is supplied at a pressure as high as 3 atm to the incubation chamber 3" through a gas inlet line 9" and discharged therefrom through a gas outlet line 10", while controlling the pressure by a pressure controller PC. A solenoid valve SV which is coupled with the pressure controller PC is used to maintain a set gas pressure. PG stands for a pressure gauge.

A gas sterilizing device, i.e., a syringe filter having a pore size of about 0.22 µm, is installed in the middle of the gas inlet line 9" to filter out microbes, thereby sterilizing the supply gas to the incubation chamber 3". Another gas sterilizing device is preferably installed in the gas outlet line 10" in order to prevent backflow of microbes in the atmospheric gas.

The incubation chamber 3" is maintained at a constant temperature which is adjusted in accordance with the type of the tissue to be cultured, e.g., 37°±0.5° C. for human liver tissues, and 38°±0.2° C., for rat or dog tissues.

As the incubation chamber of the static culture apparatus of the present invention is an erect-type which occupies a limited, small space, several sets thereof may be installed together for a simultaneous operation. Further, evaporation of the medium is minimized and no gas leakage occurs, because the incubation chamber can be tightly sealed. Therefore, the time interval for supplying the medium or the gas becomes much longer as compared with the prior art, and thus, the apparatus of the present invention may be classified as a nearly closed system.

Owing to its advantages listed above, the apparatus of the present invention may be advantageously employed in the culture of a liver tissue or a central nervous tissue, which are difficult to culture using the prior culture methods. It may be particularly useful in the field of neurological science because it is possible to culture the central nerve tissues regardless of age, i.e., the degree of differentiation.

Further, an in vitro model of human hepatitis B virus can be established by culturing the liver tissue using the culture apparatus of the present invention, because the structural integrity of hepatocyte can be maintained during the culture.

To produce antibodies it is necessary to immunize an animal through repeated injections of an antigen over a long period of time, i.e., more than one month. However, it is possible to carry out an in vitro immunization of a spleen tissue in a shortened period, by injecting the desired antigen into the tissue being cultured in the culture apparatus of the present invention. It is thus possible to obtain human monoclonal antibodies from immunized human spleen tissue.

Further, the organic tissue culture apparatus of the present invention may be used for the production of antibodies against a cancer marker protein, and the antibodies may be used for the treatment of cancer and in the gene therapy.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1

Culture of Rat Liver Tissue (1) Culture by a Dynamic Culture System

A Sprague-Dawley rat was decapitated and its liver was delivered in an aseptic state. The liver was sectioned to obtain a slice having a thickness of 260 µm and an area of 2 $mm^2$ and the liver slice was cultured using the dynamic culture apparatus of FIG. 3.

The mesh had a pore size of 260 µm and the incubation chamber was made of cylindrical glass and rotated at 7 rpm. A 95% $O_2$/5% $CO_2$ gas mixture was sterilized using a 0.2 µm filter and then introduced to the incubation chamber at 1.7 atm and a fresh gas was introduced to replace the gas phase every 10 min. The culture was carried out for 48 hours by using a medium having the following composition:

[Medium Composition] Waymouth MB 752/1 powdered medium(Gibco) 10% Fetal bovine serum(B.M.) 2.2% sodium bicarbonate(Sigma) 25 mM D-glucose(Merck) 1 µg/ml crystalline bovine zinc insulin(C.R.) antibiotics mixture(Gibco)

Half of the medium charge was replaced with a fresh medium every 12 hours.

(2) Culture by a Static Culture Apparatus

The rat liver slice obtained as in (1) was cultured using the static culture apparatus of FIG. 4.

The mesh had a pore size of 260 µm and the incubation chamber was made of square pillar-formed glass. A 95%

$O_2/5\%$ $CO_2$ gas mixture was sterilized using a 0.2 μm filter and then introduced to the incubation chamber at 1.2 atm and a fresh gas was introduced every 15 min. 20 ml of the medium of the same composition as described in (1) was placed in the medium reservoir and the timer in the medium supplying line was set to initiate the medium supply at 12 second intervals.

EXAMPLE 2

Confirmation of the Morphological and Biochemical Viabilities of the Cultured Tissue The morphological and biochemical viabilities of the tissues cultured in accordance with the methods of Example 1 (1) and (2) were confirmed by the following processes.

(1) Determination of Morphological Viability (i) Observation with an optical microscope The cultured liver tissue was taken at every 24 hours from the initiation of the culture, fixed in 10% neutral bufferred formalin, and then embedded in paraffin. The embedded tissue was sectioned in 6 μm thickness, stained with hematoxylin eosin(H & E), and then observed under an optical microscope.

Viability of the cells were determined by the criteria, e.g., acidophilic cytoplasm, condensed nucleus and loss of chromatin, which are the characteristics of dead cells.

(ii) Observation with an electron microscope

The cultured liver tissue was taken at every 24 hours from the initiation of the culture, fixed in a chilled mixture of 2% glutaraldehyde and 2% paraformaldehyde diluted with 0.1M cacodylate(pH 7.4), and then embedded in epon. The embedded tissue was sectioned in 70 nm thickness, subjected to a contrast staining with uranyl acetate and lead citrate, and then observed under an electron microscope(Jeol 1200 EX-2).

Viability of the cells were determined by the criteria, e.g., loss of cytosol, disruption of cell membrane, condensed nucleus, loss of chromatin and mitochondrial swelling, which are the characteristics of dead cells.

Viability of the cell in the cultured tissue and that of tissue slice having a cell viability of more than 50% were calculated from the following equations:

$$\text{Viability(area) (\%)} = \frac{\text{Area of viable tissue } (\mu m^2)}{\text{Area of cultured tissue } (\mu m^2)} \times 100$$

$$\text{Viability(slice) (\%)} = \frac{\text{No. of viable tissue } (\mu m^2)}{\text{No. of cultured tissue } (\mu m^2)} \times 100$$

(iii) Result

When the tissue which was cultured for 48 hours was observed under an optical microscope, clear nucleolus and basophilic cytoplasm were found in viable cells, while extremely condensed nucleus and acidophilic cytoplasm were found in dead cells. In the longitudinal and cross sections of the H & E-stained culture tissues, no central necrotic band was observed and all of the cells in the gas-tissue interface and medium-tissue interface were alive.

When the same tissue was observed under an electron microscope, extremely condensed nucleus, loss of chromatin, loss of cytosol, disruption of cell membrane, and serious mitochondrial swelling were observed in dead cells, while the alive cells were indistinguishable from the non cultured group.

The morphological observations showed that the average values of the viability(area) and the viability(tissue slice) were good, about 70 to 80% and about 70 to 75%, respectively.

(2) Determination of Biochemical Viability (i) LDH(lactate dehydrogenase) activity 100 μl samples of the culture solution were taken at 5, 10, 30, and 60 minutes from the initiation of culture, and thereafter, every 2 hours. The activity of LDH released to the culture solution was measured with a UV spectrophotometer (Unicam), while the protein content of the culture tissue was determined by Lowry method. The LDH activity was expressed in unit/g protein.

(ii) ATP and DNA content of the tissue slice

Ten cultured tissue samples were taken at every 2 hours from the initiation of the culture, weighed, homogenized, and then centrifuged. Slice ATP content/g wet weight of the supernatant was determined with a spectrophotometer using an ATP measuring kit(Sigma). The DNA content of the culture tissue was determined from the amount of the precipitate formed using DAP(4',6-diamidino-2-phenylindole).

(iii) Result

With the lapse of culture time, the LDH activity in the culture solution increased from 170 at 5 min. to 200 at 60 min. from the initiation of culture, and LDH activities measured after 3 hours from the initiation of culture were unchanged at about 200, while the LDH activity of the control group, which was cultured for 6 hours and thereafter left standing at room temperature, was observed to increase continuously with time.

ATP and DNA contents in the tissue were nearly constant over a period of 48 hours, showing no statistic significance.

The above results show that the tissue can be successfully cultured using the culture apparatus of the present invention, showing little morphological difference from the non-cultured tissue and no sign of central necrosis. Further, cultured tissue can be functionally preserved as is shown by the biochemical confirmation that the LDH activity and ATP and DNA contents are nearly the same as those of the control group.

EXAMPLE 3

Culture of Central Nervous Tissue (Step 1) Experimental Animal and Culture Tissue Male and female rats were mated and the vaginal plug was examined the next day to obtain a basis for calculating the pregnancy period. The pregnant rat was sacrificed at every-day period from the 15th day of pregnancy to the end of pregnancy, and a fetus was separated therefrom. The fetus was decapitated and its brain was aseptically delivered under a 3-D microscope. The delivered brain was cut into three serial coronal slices by using a mechanic tissue slice maker. The first slice was treated for tissue culture; the second slice, for the observation under an optical and an electron microscopes; and the third slice was stored in a liquid nitrogen tank for biochemical analysis.

Young rats of neonatal 1 to 5 days were treated according to the same procedures as above.

Mature rats were anesthetized by injecting peritoneally 0.04 cc/100 g body weight of sodium pentobarbital, their skulls were opened to rapidly deliver their brains, and then the brains were treated according to the same procedures as above. In case of mature rats, their spinal tissues were also taken.

(Step 2) Tissue culture

The tissues obtained in above (Step 1) were cultured using the culture apparatus of FIG. 4 under the following conditions.

(i) Medium for tissue culture

The following media were used for tissue cultures while varying the composition in accordance with the type of the culture tissue.

Medium comprising fetal serum

10% Fetal bovine serum*[1]

Dulbeco's Modified Eagle's Medium

Waymouth MB 752/1 medium containing L-glutamine 2.24 g sodium bicarbonate

A mixture of 100 µg/ml streptomycin and 100 IU/ml penicillin 4.5 g D-glucose 12.5 mM-15 mM HEPES buffer*[2]

0.05–1% reduced glutathione*[2]

(Note: *[1] used after dialyzing with a bag having a cut-off value of 80,000 daltons to remove low molecular-weight molecules, when culturing young tissue aged less than 1 day; while used as it was, when culturing tissue aged more than 1 day. *[2] concentration thereof was increased in accordance with the increase in gas pressure.

Medium without fetal serum

Dulbeco's Modified Eagle's Medium

Waymouth MB 752/1 medium containing L-glutamine 2.24 g sodium bicarbonate

A mixture of 100 µg/ml streptomycin and 100 IU/ml penicillin 4.5 g D-glucose

10–25 mM HEPES buffer 0.05–1% reduced glutathione

Supplement*[1]

10–50 µg/l transferrin

5–20 µg/l insulin

1–5 nM hydrocortisone

Trace amounts of NGF, EGF, PDGF and FGF

Trace amounts of insulin-like growth hormone

1–6.5 ng/ml progesterone

1–5 mM L-glutamine (Note: *[1] The amount of each component was regulated in accordance with the age of the tissue to be cultured, i.e., amounts of the components were gradually decreased from maximal amounts, as the tissue become aged.)

(ii) Regulation of gas pressure

In culturing the central nervous tissues, the gas pressure was regulated in the following manner. In case of the fetal or initial neonatal group, the gas pressure was increased continuously from 0.8 kgf/cm$^2$, but not to exceed 1.2 kgf/cm$^2$. In case of the mature group, the gas pressure was increased continuously from 1.0 kgf/cm$^2$, and when the gas pressure exceeds 1.5 kgf/cm$^2$, 0.05–1.0% of reduced glutathione was added to the apparatus.

(Step 3) Confirmation of Morphological and Biochemical Viabilities of the Culture Tissue The morphological and biochemical viabilities of the cultured tissues were confirmed in accordance with the method of Example 2, the viability(area) and viability(tissue slice) figures obtained from morphological observations as well as the viability determined by biochemical observations were all excellent. Specifically, when the cells of the tissue cultured for 6 hours were stained with cresyl violet and then observed by a light microscope, it was found that the RNAs of cultured cells, i.e., Nissle bodies in perikaryons, were recovered to the same level as that of non-cultured tissue.

EXAMPLE 4

Culture of Hepatitis B Virus (Step 1) Preparation of the Culture Medium

A medium has the same composition as that of Example 1 for the culture of a liver tissue, except that 0.05–0.09 g/100 ml medium of reduced glutathione(Sigma®) was added thereto, was prepared. The biopsy liver of a patient with hepatitis B surface antigenemia was incubated in the above medium at 4° C. for more than 2 hours to release hepatitis B viruses into the medium. The resulting culture medium containing released viruses was used as a source of virus.

(Step 2) Culture of Liver Tissue

A rat liver tissue slice having 260 µm thickness was cultured in accordance with the same method of Example 1 by using the culture apparatus of FIG. 4 and the culture medium prepared in (Step 1) which contains hepatitis B viruses.

(Step 3) Confirmation of Hepatitis B Virus Infection in the Cultured Liver Tissue Infection of the cultured tissue of (Step 2) with hepatitis B virus can be confirmed by using antibodies against HBsAg or HBcAg which are always present in the tissue infected with hepatitis B virus. Infection of virus was confirmed by an increase in the HBsAg titer of cultured tissue with the lapse of culture time, in contrast to the HBsAg titer of non-cultured viral source tissue.

The titers of hepatitis B virus surface antigen in the culture media, which was cultured for 6, 12 and 24 hours, respectively, were measured using EIA method(Abbott, U.S.A.). As a result, the infected culture media showed rapidly increasing titers of hepatitis B virus surface antigen, as about two folds at 6 hours from the initiation of the culture. However, the control media, which was cultured without hepatitis B virus, showed no change in the titer.

The presence of viral DNA in cultured tissue was determined by dot-blot analysis using $\alpha$-$^{32}$P-BamHI fragment of plasmid pAM6(ATCC 40101) as DNA probes and glyceraldehyde-3-phosphate dehydrogenase(GAPDH) DNA as a control. As a result, intense spots of viral DNA were observed in cultured tissues, and the amount of viral DNA in the 12-hour incubated tissue increased by about 1.7-fold in compared to that of 6-hour incubated tissue.

The presence of viral surface and core antigens were investigated by an immunohistochemical staining method. In the light microscopic observations, surface and core antigens were observed to be intensely stained on their cytoplasm and nuclei, respectively.

In addition, viral antigens and Dane particles were investigated under an electron microscope(Jeol 1200 EX-2), where multiple long filamentous surface antigens and Dane particles measuring about 50 nm in diameter were observed.

EXAMPLE 5

Production of Antibodies

A cross-sectional slice of mouse spleen having a 400–500 µm thickness was cultured in accordance with the same method as in Example 1 by using the culture apparatus of FIG. 4. The composition of the medium used in this experiment was the same as the medium without FBS of Example 3, while it contained as supplements insulin and insulin-like growth hormone only.

A human hepatitis B viral vaccine, e.g., Hepavax®(Green Cross, Korea) containing 0.2–2 µg of protein, was added to the medium after 2 hours from the initiation of culture.

The titer of anti-HBsAg antibodies in the cultured tissue was determined in accordance with the EIA method (Abbott). As a result, the titer of anti-HBsAg antibodies was 2.6 mIU/ml for 6-hour cultured tissue; 3.5 mIU/ml, for 12-hour cultured tissue; and 2.1 mIU/ml, for 12-hour cultured tissue, while the cut-off value was 2.1 mIU/ml. On the other hand, the concentration of HBsAg in the medium decreased with the lapse of culture time, and about 30–35% decrease in HBsAg concentration was observed at 18 hours from the initiation of the culture.

In addition, the amount of precipitated Ag-Ab complex increased steadily with culture time. The Ag-Ab complexes were collected and then separated into antigens and antibodies. The antibodies were mainly composed of IgM type, which is confirmed from the result that more than 90% of antibodies bound to rabbit anti-IgM IgG.

The cultured tissue was ground to separate cells, which were fused with cells of myeloma cell line($P_3 \times 63$ Ag.8 V653; ATCC CRL 8006). The fused cell was cultured and screened to obtain monoclonal antibodies.

Human monoclonal antibodies can be obtained by displacing the mouse spleen tissue with human spleen tissue and fusing the cells from the cultured human spleen tissue with the cells of human non-secretory myeloma cell line, e.g., SKO-007(HAT sensitive, ATCC CRL 8033-1).

While the invention has been described with respect to the specific embodiments, it should be recognized that various modifications and changes may be made by those skilled in the art to the invention which also fall within the scope of the invention as defined by the appended claims.

What is claimed is:

1. A method for culturing an organic tissue slice in an oxygenated gas under the supply of a liquid culture medium comprising the steps of: attaching the tissue slice onto an inner side of a mesh which is placed in a static erect incubation chamber so as to form a layer of open space having a substantially uniform thickness between the inner wall of the chamber and the mesh wherein the mesh is made of stainless steel and has a mesh size ranging from 200 to 400 µm and the mesh substantially conforms to the shape of the inner wall and the thickness of the layer of open space between the inner wall of the chamber and the mesh ranges from 2 to 3 mm; and culturing the tissue in the presence of the oxygenated gas while supplying the culture medium to the top of said layer at regular intervals so that the tissue is exposed alternately to the medium and gas at a contact time ratio in a range from 1:2.5 to 1:3.5.

2. The method of claim 1, wherein the mesh is of a square or a cylindrical pillar form.

3. The method of claim 1, wherein the tissue is a liver tissue or a central nervous tissue.

4. The method of claim 1, wherein the oxygenated gas is a mixture of 95% by volume $O_2$ and 5% by volume $CO_2$.

* * * * *